United States Patent
Whitlock et al.

(10) Patent No.: US 7,401,529 B2
(45) Date of Patent: Jul. 22, 2008

(54) METHOD AND SYSTEM FOR STANDARDIZED CLASSIFICATION OF UNDERGARMENTS

(75) Inventors: Leslie Whitlock, Cherryville, NC (US); Monica Bentley, Hiddenite, NC (US); Cal Rossi, Huntersville, NC (US)

(73) Assignee: HBI Branded Apparel Enterprises, LLC, Winston-Salem, NC (US)

( * ) Notice: Subject to any disclaimer, the term of this patent is extended or adjusted under 35 U.S.C. 154(b) by 29 days.

(21) Appl. No.: 10/910,959

(22) Filed: Aug. 4, 2004

(65) Prior Publication Data

US 2005/0097967 A1     May 12, 2005

Related U.S. Application Data

(60) Provisional application No. 60/492,873, filed on Aug. 6, 2003, provisional application No. 60/492,737, filed on Aug. 6, 2003.

(51) Int. Cl.
*G01N 3/02* (2006.01)
(52) U.S. Cl. ........................................ 73/856
(58) Field of Classification Search .......... 73/856–860, 73/826–837, 159, 794, 779
See application file for complete search history.

(56) References Cited

U.S. PATENT DOCUMENTS

| | | | |
|---|---|---|---|
| 1,817,617 A | | 8/1931 | Gosch |
| 2,187,914 A | | 1/1940 | Reitan |
| 2,706,402 A | | 4/1955 | Jones |
| 3,444,728 A | | 5/1969 | Burns |
| 3,471,068 A | | 10/1969 | Foreman |
| 3,730,405 A | * | 5/1973 | Ezell et al. .................... 223/72 |
| 3,879,990 A | | 4/1975 | Joy |
| 4,136,557 A | * | 1/1979 | Bell et al. ...................... 73/816 |
| 4,245,512 A | * | 1/1981 | Saunders ....................... 73/789 |

(Continued)

FOREIGN PATENT DOCUMENTS

DE     003434068 A1     3/1986

(Continued)

OTHER PUBLICATIONS

L.L.Bean Catalog, Spring 2004, pp. 59,64,65, and 67, no date.

(Continued)

*Primary Examiner*—Jewel V Thompson
(74) *Attorney, Agent, or Firm*—Womble Carlyle Sandridge & Rice, PLLC (57) ABSTRACT

The clamps of the present invention are initially placed apart with a specific separation to properly hold the garments in the constant rate of expansion (CRE) machine. The test method preferably uses panties that have been prepared according to specific test criteria and the CRE machine pre-programmed with specific parameters including the preload and the initial rate of extension. Before testing commences, the midpoint of an individual panty is placed at the center of the clamps. After a pre-determined resistance is sensed by the CRE machine, the rate of extension and the load instantly increase to test the panty's percent of elongation and modulus. This method is repeated for several styles and sizes of panties to obtain accurate, consistent elongation and modulus measurements for each style and size. These measurements thus categorize all of the measured styles and sizes into a standardized panty support classification system.

20 Claims, 9 Drawing Sheets

U.S. PATENT DOCUMENTS

| | | | |
|---|---|---|---|
| 4,873,878 A * | 10/1989 | Milton | 73/865.8 |
| 5,094,110 A | 3/1992 | Porter et al. | |
| 5,123,175 A * | 6/1992 | van der Kuur | 33/789 |
| 5,235,860 A | 8/1993 | Horton et al. | |
| 5,541,394 A | 7/1996 | Kouchi et al. | |
| 5,605,739 A | 2/1997 | Stokes et al. | |
| 5,659,740 A | 8/1997 | Ezaki et al. | |
| 5,944,237 A | 8/1999 | Gouldson | |
| 6,381,510 B1 | 4/2002 | Amidhozour et al. | |
| 6,487,902 B1 * | 12/2002 | Ghosh | 73/159 |
| 6,493,678 B1 | 12/2002 | Foster et al. | |
| 6,665,577 B2 | 12/2003 | Onyshkevych et al. | |
| 2003/0114810 A1 | 6/2003 | Weber | |
| 2003/0125695 A1 | 7/2003 | Dorschner | |
| 2003/0130905 A1 | 7/2003 | Foster et al. | |
| 2003/0135186 A1 | 7/2003 | Olson et al. | |

FOREIGN PATENT DOCUMENTS

| | | |
|---|---|---|
| JP | 411061635 A | 3/1999 |
| JP | 02001113100 A | 4/2001 |

OTHER PUBLICATIONS

Elite Home Medical Supplies Order Form (Jobst Opaque Support Stockings), no date.
Elite Home Medical Supplies Order Form (Compression Hosiery Product Usage Chart), no date.

* cited by examiner

| LIGHT | MODERATE | FIRM |
|---|---|---|
| 0318  H021 | 0802 | 0335  0378 |
| 0390  H051 | 0831 | 0336  0388 |
| 0391  H062 | 0832 | 0345  0395 |
| 0393  H091 | 0847 | 0349  0791 |
| 0394 |  | 0374  0792 |
|  |  | 0375 |

*FIG. 10a*

| 1 | 2 | 3 | 4 | 5 | 6 |
|---|---|---|---|---|---|
| 0390 | 0391 | 0374 | 0378 | 0318 | 0335 |
| 0393 |  | 0375 | H051 | 0349 | 0336 |
| 0394 |  | 0395 | H062 | 0802 | 0345 |
|  |  | H021 | H091 | 0831 | 0388 |
|  |  |  |  | 0832 | 0791 |
|  |  |  |  | 0847 | 0792 |
|  |  |  |  | HSH003-2 |  |

*FIG. 10b*

Control Trust System™

Our extensive fit and stretch testing assures consistent levels of support for control you can trust.

| Light | Moderate | Firm |
|---|---|---|
| Everyday Smoothing | Shaping and Lifting | Maximum Control and Support |
| 1  2 | 3  4 | 5  6 |

*FIG. 11*

METHOD AND SYSTEM FOR STANDARDIZED CLASSIFICATION OF UNDERGARMENTS

This application claims the benefit of U.S. Provisional Patent Application Ser. No. 60/492,873 and Provisional Patent Application Ser. No. 60/492,737, both filed on Aug. 6, 2003, the contents of which are incorporated by reference herein.

BACKGROUND OF THE INVENTION

1. Field of the Invention

The present invention relates generally to a standardized method of testing and classifying undergarment control. More particularly, the present invention relates to a standardized method of testing undergarment control using a clamp mechanism in a commercially available machine and a resultant standardized classification of undergarment control.

2. Description of the Related Art

Undergarments, specifically women's panties, are advertised with respect to the level of support they provide to the wearer. The three general classifications used to describe the level of support for women's panties are light, moderate and firm support. Women purchase these garments with the belief that the product will perform in accordance with its advertised level of support. Underlying their decision to purchase a panty of a particular support level, is the belief that the panty has been tested to perform as advertised. However, there does not exist a standard method to test the level of support that women's undergarments, specifically panties, provide to the wearer. Thus, there does not exist a standard classification system of undergarment control.

Undergarment manufacturers may test the level of support of the component materials that are assembled to make the garments. However, these materials are tested only before the materials are assembled and sewn together as a completed garment, such as a panty. There is no further machine testing to determine the level of support that the finished garment provides.

Currently, women's undergarment manufacturers test the support of panties by using an empirical method. Testers put their two fists in the hole openings for the legs and move their arms apart. Based on the level of resistance to stretching that the tester senses, the panty is classified as a light, moderate or firm support garment. This sort of empirical testing method is not scientific, consistent or repeatable. The tester may place his/her fists at different locations inside different panties during successive tests. The tester may also use different forces to separate his/her arms while testing the same panty or different panties. Further, the tester may not use a constant rate of expansion as his/her arms open with the same panty or with different panties. Also, the tester may fatigue during the testing of a number of panties and thereby improperly report a higher level of resistance than he/she would have reported during earlier testing of the same panty or of different panties. These variables prevent accurate standardized measurement and classification of the support levels of panties. Essentially, the human element in the test makes the current test method unreliable.

A need therefore exists for a standardized testing method to accurately determine the level of support of panties and a standardized classification system for the level of support provided in such panties.

SUMMARY OF THE INVENTION

It is an object of the present invention to provide a pair of clamps to hold panties at a uniform location from which measurements on a number of panties are taken.

It is an object of the present invention to provide a pair of clamps having a specific configuration.

It is another object of the present invention to properly align the panties prior to testing to provide accurate measurements.

It is still another object of the present invention to stretch the panties using a consistent force to obtain a consistent elongation and modulus when measuring.

It is yet another object of the present invention to use a test method that provides a pre-load to remove the variability from measurements.

It is still yet another object of the present invention to use consistently accurate objective measurement criteria to properly measure the panties.

It is a further object of the present invention to classify the panties according to their support level.

It is a further objective of the present invention to provide a classification system that accurately represents the advertised level of undergarment support.

It is still a further object of the present invention to preprogram the test device with specific parameters.

These and other objects and advantages of the present invention are achieved by an automated device used to measure and the standardized test method of the present invention. The clamps of the present invention are preferably mounted in a standard commercially available constant rate of extension (CRE) machine. The clamps of the present invention are placed with a specific separation in the CRE machine to properly hold the garments in preparation for testing. The test method uses panties that have been prepared according to specific test criteria and the CRE machine preprogrammed with specific parameters.

Before testing commences, the midpoint of an individual panty side is placed at the center of one of the clamps. The CRE machine is preprogrammed to have a specific preload and a specific rate of extension between the clamps when the clamps first commence separation. After a pre-determined resistance is sensed from the panty sides by the CRE machine, the rate of extension and the load instantly increase to test the panty's percent of elongation and modulus. This method is repeated for several styles and sizes of panties to obtain accurate, consistent elongation and modulus measurements for each style and size. These measurements thus categorize all of the measured styles and sizes into a standardized panty support classification system.

BRIEF DESCRIPTION OF THE DRAWINGS

The foregoing and still other objects and advantages of the present invention will be more apparent from the following detailed explanation of the preferred embodiments of the invention in connection with the accompanying drawings.

DETAILED DESCRIPTION OF THE INVENTION

Figure 1:
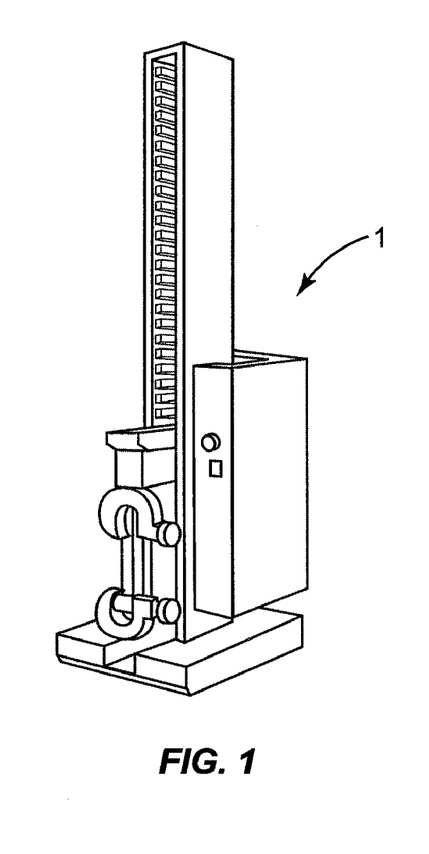
FIG. 1 illustrates a perspective view of a commercially available testing machine.

Referring to the drawings and in particular, FIG. 1, there is provided a commercially available constant rate of extension (CRE) machine generally represented by reference numeral 1. The CRE machine 1 is used to determine the percent of elongation and modulus of a garment especially a panty when it is stretched at a constant rate of extension according to testing criteria. The CRE machine 1 increases the length of the panty at a constant rate, thus ensuring accurate and repeatable results. The CRE machine 1 is equipped with an automatic recording device and a cycling control. Also, the CRE machine 1 can be pre-programmed to run according to specific parameters.

The testing machine 1 must also be programmed according to specific parameters. The parameters are defined below:
Pre-Flex cycles=0
Clamp to clamp separation=279.5 mm
Pre-load=0.1 kg
Pre-load Speed=350 mm/min
Test Load=4.0 kg
Test Speed=508 mm/min According to a preferred embodiment of the invention, a commercially available Zwick™ CRE test machine model Zwick™ 1446 is used. It should be noted that other analogous CRE machines could be used provided they can accept clamps 2 and 3 of FIG. 2, and also provide reliable consistent elongation and tension of garment during repeated testing.

Prior to testing, the panties and the CRE machine 1 must be prepared. Each panty is relaxed on a flat surface at a standard atmospheric condition of 70° F.±2° F. temperature (or 21° C.±1° C.) and 65%±2% relative humidity. After the panties have been in this condition for a minimum of four hours, they are proper for textile testing. Before actual testing of each properly prepared panty, the tester will confirm the effective weight, number of cycles, outgoing/incoming curve and modulus points, to be read for each sample.

Following panty preparation, CRE machine 1 must be pre-programmed according to certain parameters. Prior to stretching the panty, the initial pre-load and rate of extension of CRE machine 1 are set at low levels. The initial clamp extension occurs at these low levels until CRE machine 1 senses a pre-determined level of resistance from the sides of the panty. Then, the test load and the speed of separation in between the clamps increase sharply. Several different panty styles and sizes are tested to obtain the test results and the necessary information for the new support classification system.

Figure 2:
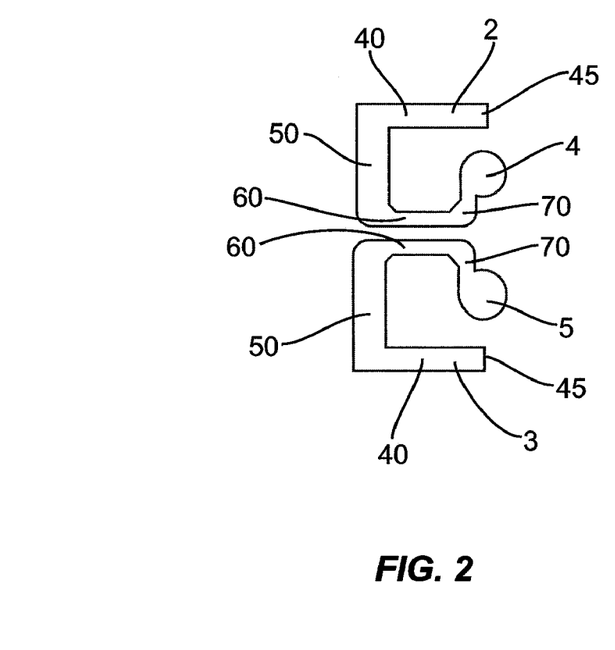
FIG. 2 illustrates a front view of the clamp pair of the present invention.

Referring to FIG. 2, clamps 2 and 3 are placed in CRE machine 1. Clamps 2 and 3 have almost a square or rectangular shape. Each clamp 2, 3 has a securing arm 40, a vertical arm 50 basically perpendicular to the securing arm, and thin a arm 60 basically perpendicular to the vertical arm and basically parallel to the securing arm. Each arm 60 has a small stem or arm 70 basically perpendicular to thin arm 60 and basically parallel to vertical arm 50. Small arm 70 has an enlarged head 4 (clamp 2) or head 5 (clamp 3) that is spaced from securing arm 40. Thus as shown in FIG. 2, clamps 2 and 3 provide a configuration in which heads 4 and 5 opposite each other such that the heads have their distal outer surfaces facing away from each other. Further, the center of each clamp 2, 3 when vertically aligned is just within the free end 45 of securing arm 40.

In an initial condition as shown in FIG. 2, the distance between the upper outer surface of head 4 of clamp 2 and the lower outer surface of head 5 of clamp 3 is 10 inches or 254 mm. This spacing ensures consistent alignment of different garments, especially panties, on CRE machine 1 during testing. Proper alignment ensures that measurements of panty elongation and modulus are taken from the same location on the different styles and sizes of panties during repeated tests.

Figure 3:
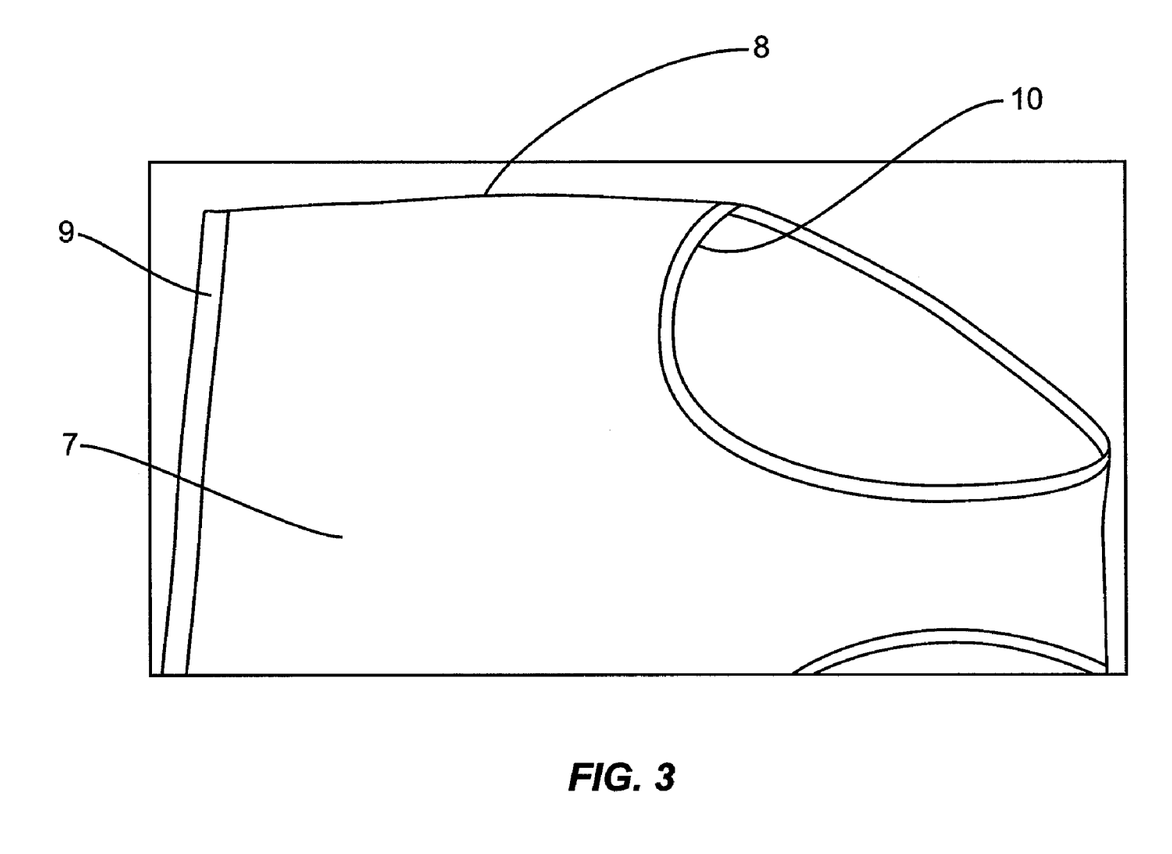
FIG. 3 illustrates a top view of a test garment of the present invention.
Figure 4:
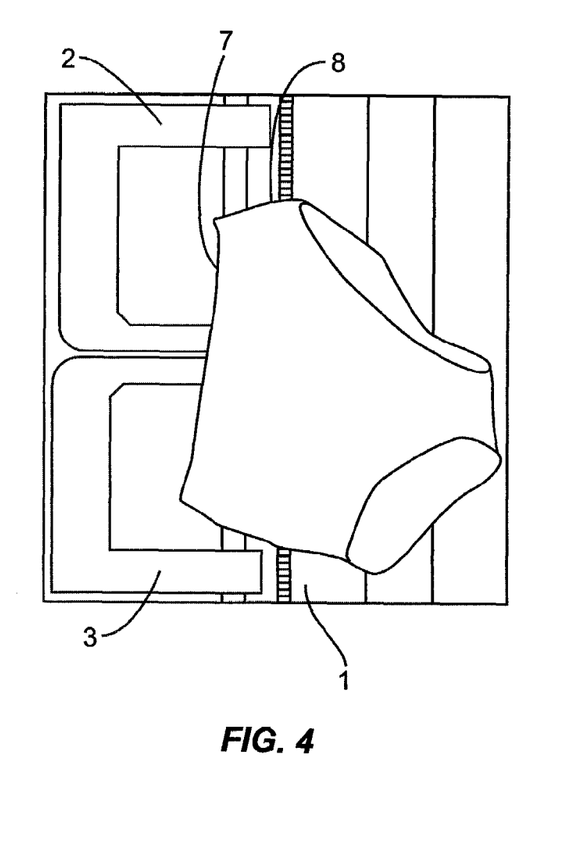
FIG. 4 illustrates a view of the garment mounted on the test machine before testing according to the method of the present invention.
Figure 5:
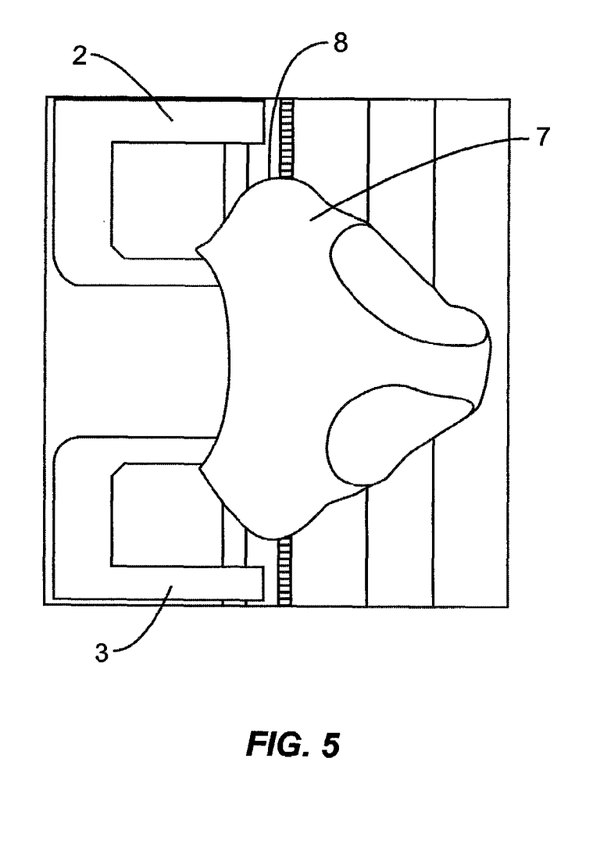
FIG. 5 illustrates a view of the garment mounted on the test machine during testing according to the method of the present invention.

Referring to FIGS. 3 to 5, a panty 7 is placed on clamps 2 and 3. The panty 7 is placed such that its center point 8, located at the midpoint of the top waistband 9 and the top of the elastic leg hole 10, is placed at the center of clamp 2 of CRE machine 1. If the measurement between the top of waistband 9 and bottom of leg elastic is more than 8 inches, the center of clamp 2, is placed 4 inches below the top of the waistband. The ultimate elongation test results should be reported to the nearest 0.1% of elongation.

Referring to FIG. 4, panty 7 is mounted on clamp 2 in the non-test position. Only center point 8 of panty 7 is in contact with clamp 2. Initially when CRE machine 1 is started, the pre-load is 0.1 kg and rate of expansion between clamps 2 and 3 is 350 mm/min.

In CRE machine 1, clamp 3 is held in a fixed position while clamp 2 moves away from clamp 3. However, clamp 3 can be movable, while clamp 2 is stationary or clamps 2 and 3 can be movable towards and away from each other depending on the standard commercial machine or device used to employ clamps 2 and 3.

Referring to FIG. 5, both sides of panty 7 are in contact with clamps 2 and 3 and the panty is in the test position. Once machine 1 senses a pre-determined resistance, between both clamps 2 and 3, the load instantly increases to 4 kg and the rate of extension between the clamps increases to 508 mm/min. The use of a 4 kg load ensures the most consistent elongation and modulus of the sample panty 7. This level of force also eliminates the need to use different loads across multiple sizes of panties.

Figure 6:
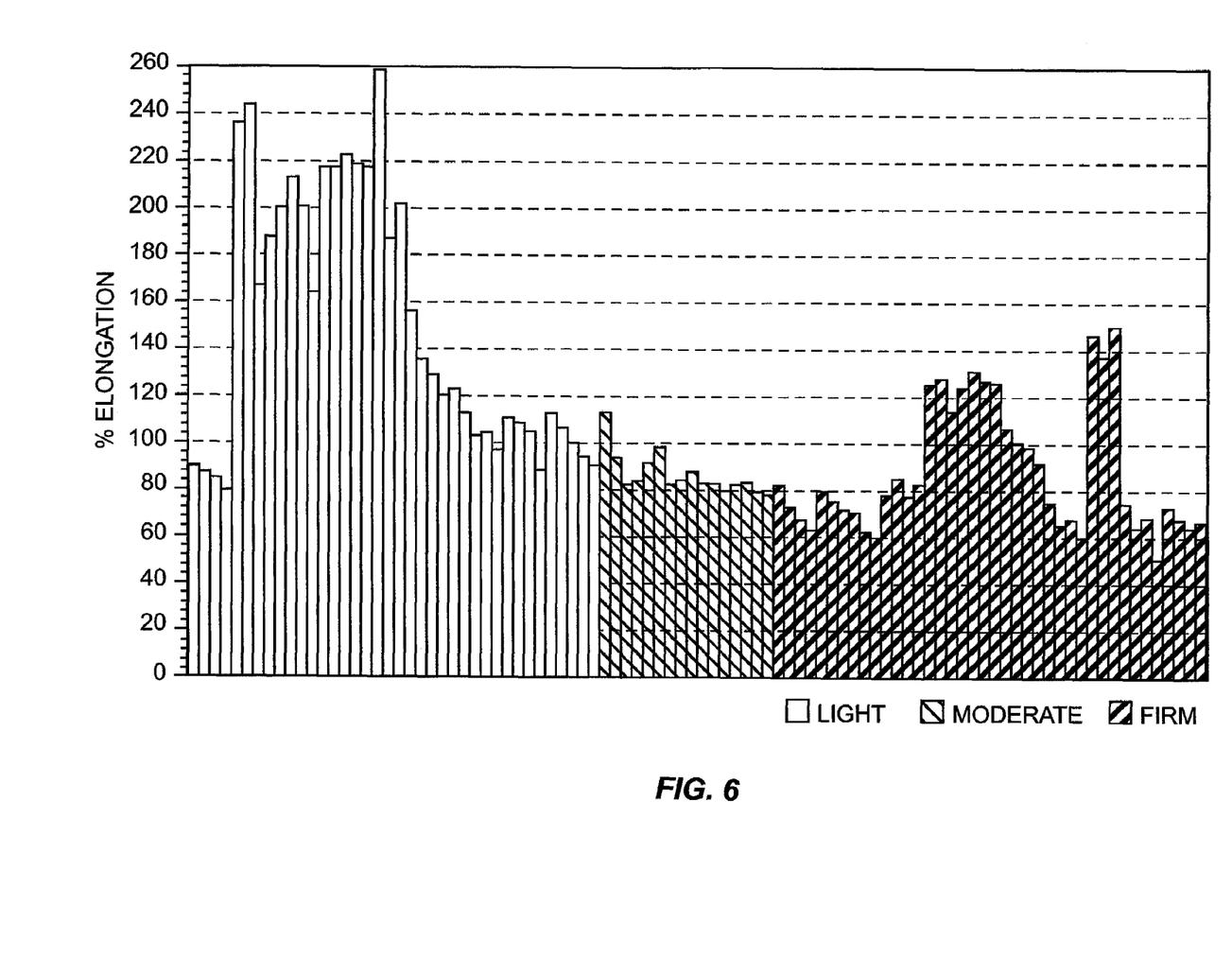
FIG. 6 illustrates the percent of elongation of all styles and sizes sorted by the current support category according to the results of the present invention.

Referring to FIG. 6, the results show selected styles and sizes grouped and classified as light, moderate and firm support. The graph shows sporadic percentages of elongation within the light support category. Similarly, the styles and sizes in the moderate and firm support categories show sporadic percentages of elongation in respective categories.

Figure 7:
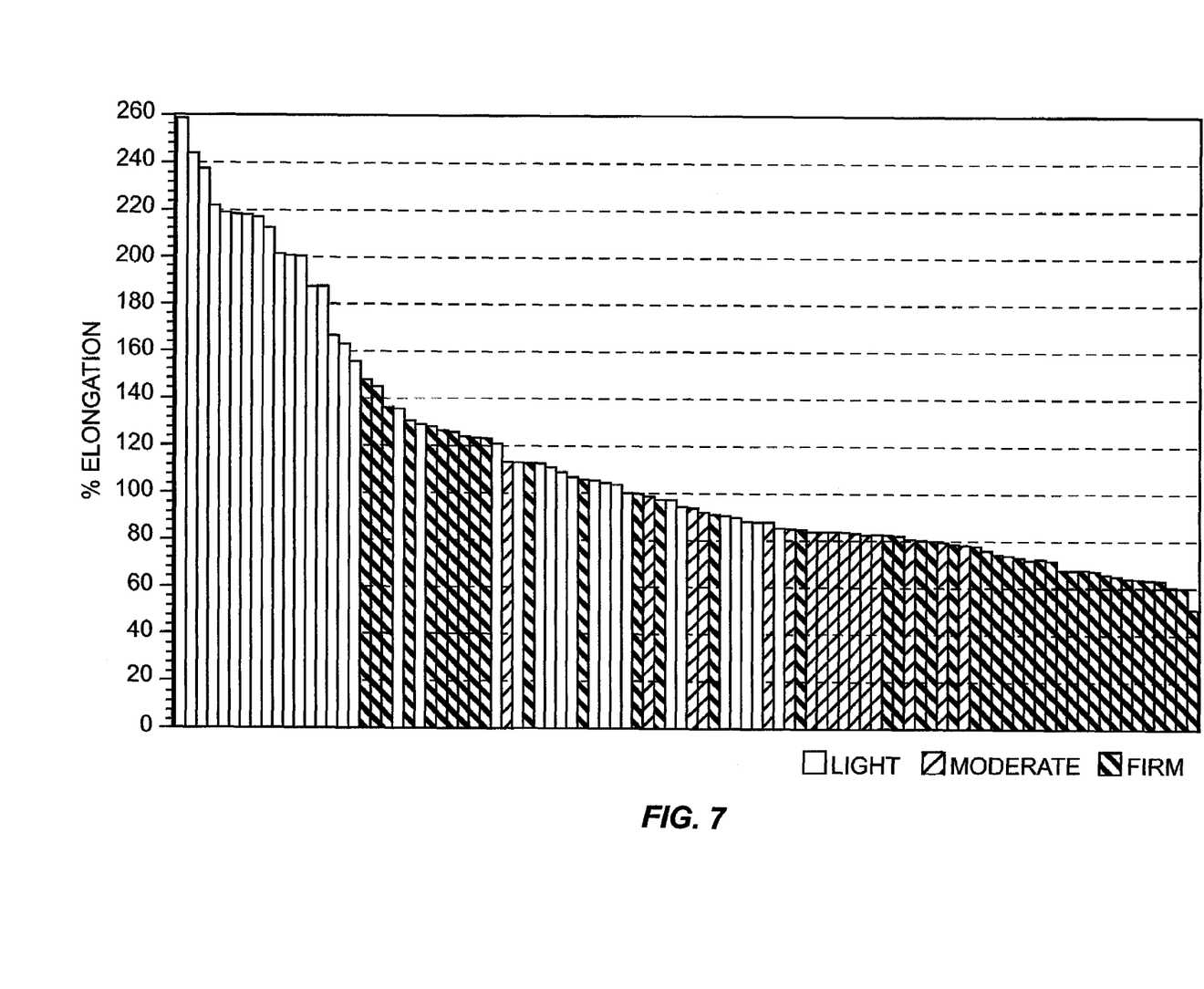
FIG. 7 illustrates the percent elongation of all styles and sizes sorted by current support category value according to the results of the present invention.

Referring to FIG. 7, the results of FIG. 6 are reclassified according to percentage of elongation independent of the panty size, style or category. The different shades of the bar graph indicate that percentages of elongation vary substantially in a support category.

Figure 8:
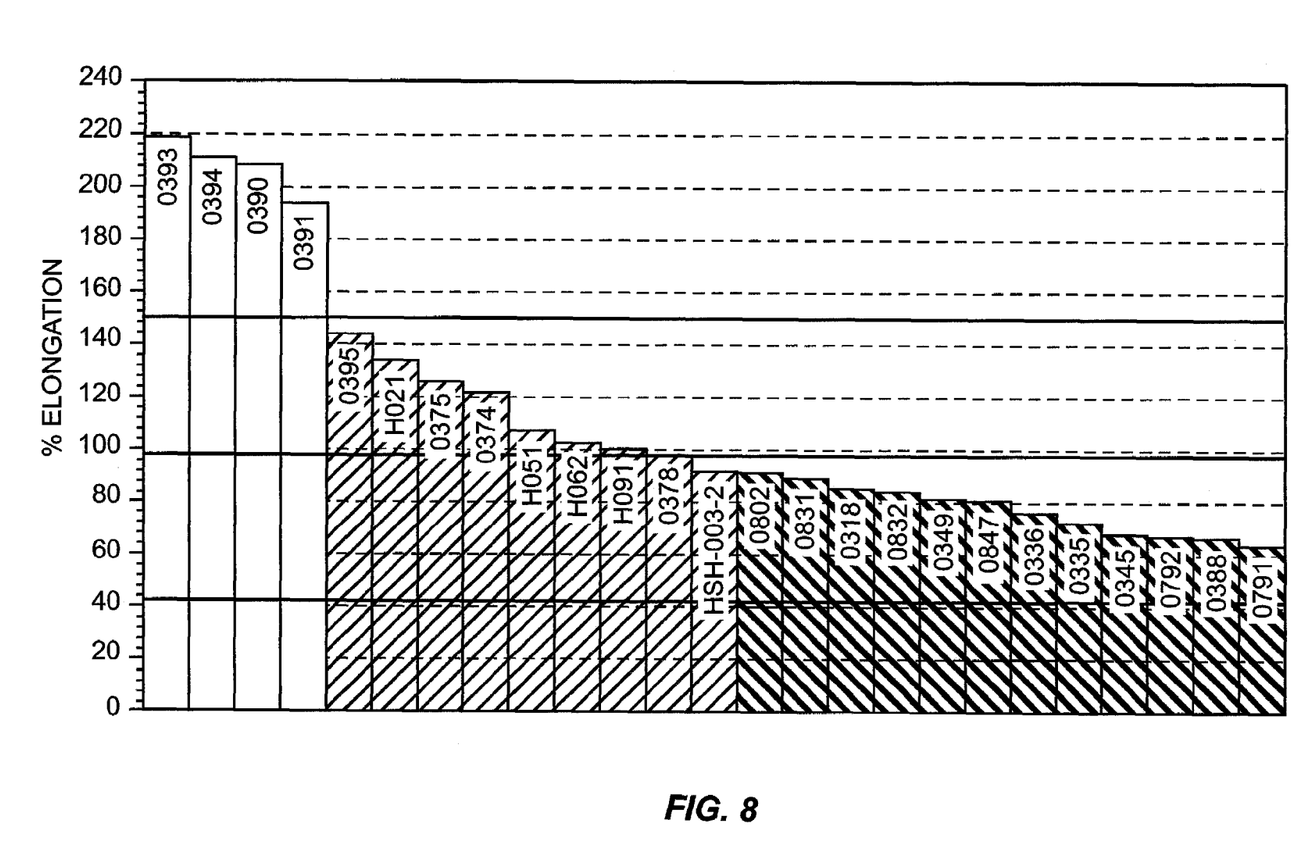
FIG. 8 illustrates the elongation average of sizes when they are reclassified according to current classifications of light, moderate and firm support.

Referring to FIG. 8, the elongation averages of the panties have been reclassified according to the level of support of the current classification system.

Figure 9:
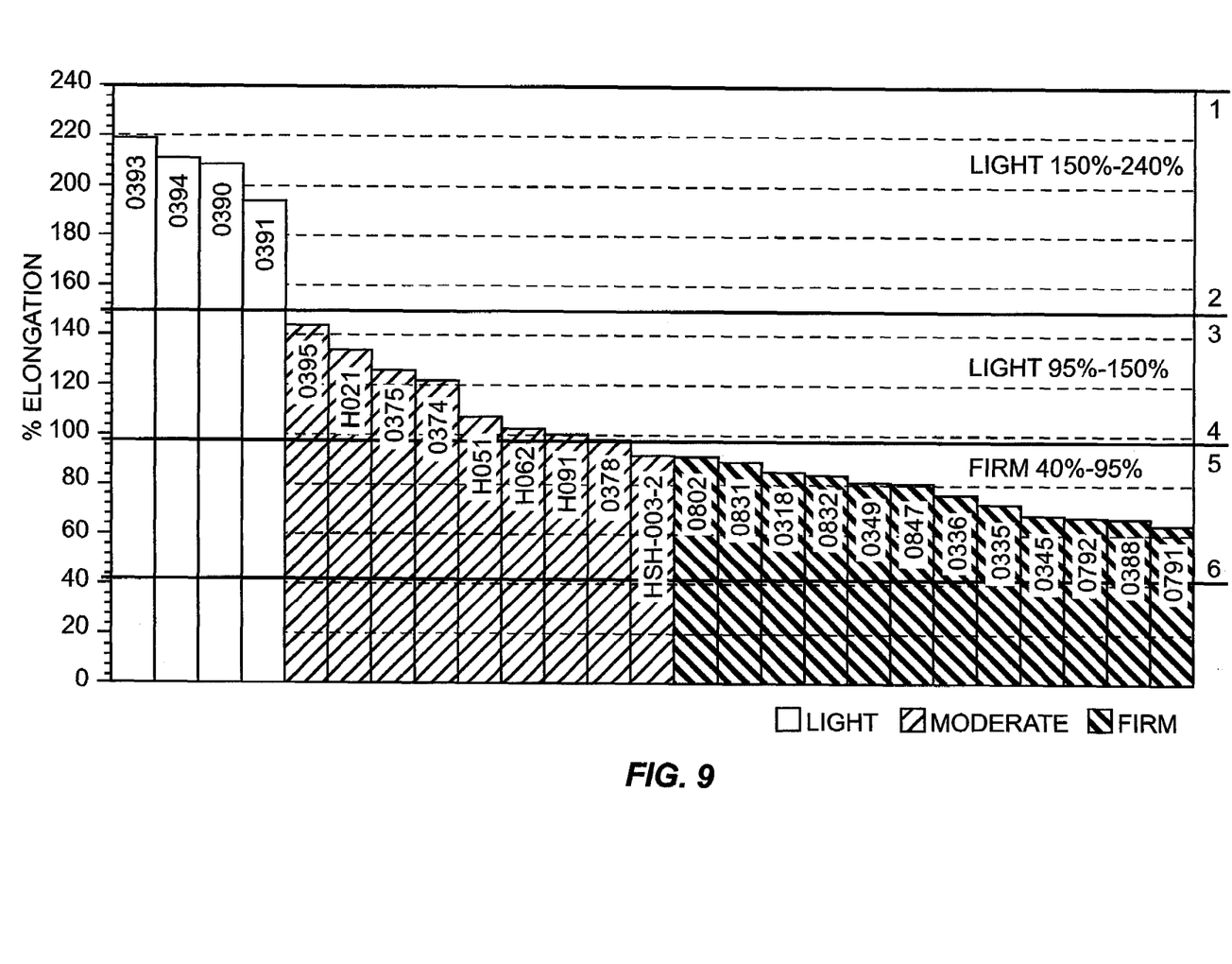
FIG. 9 illustrates the elongation average of sizes when they are reclassified as light, moderate and firm support according to the new classification system according to the present invention.

Referring to FIG. 9, the same chart is reclassified according to a new classification system. The new classification system classifies the panties from 1 representing light support to 6 representing firm support. As shown in this Figure, light support has a range of 150% to 240% elongation, moderate support has a range of 95% to 150% elongation, while firm support has a 40% to 95% elongation.

Figure 10A:
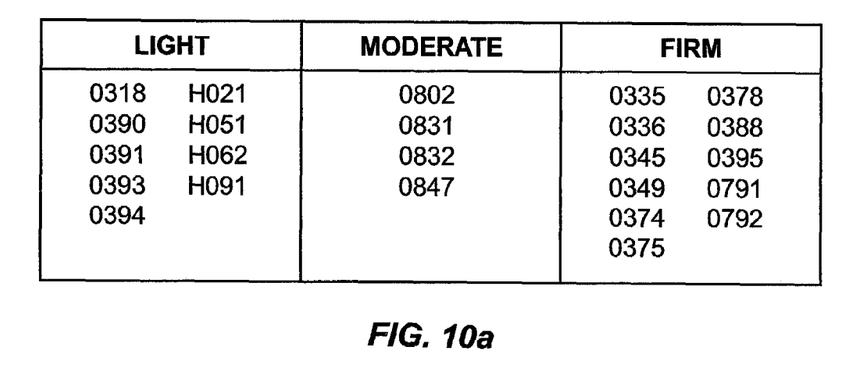
FIG. 10a illustrates the classification of different representative model numbers and sizes of panties according the current system.
Figure 10B:
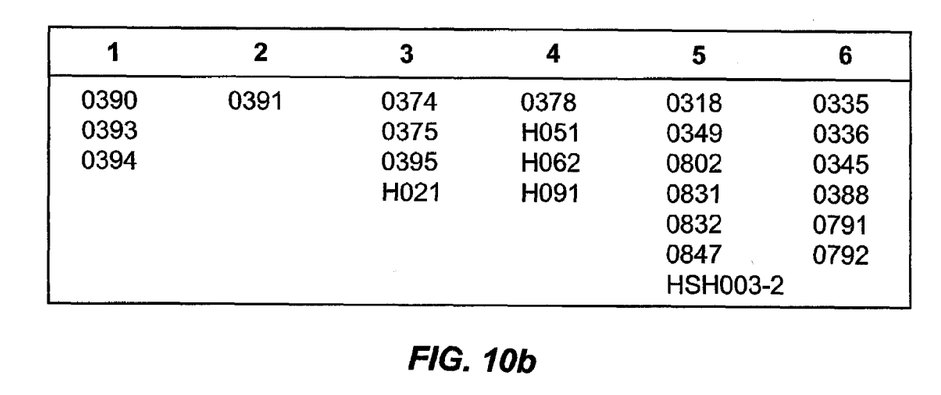
FIG. 10b illustrates the classification system different representative model numbers and sizes according the new classification system of the present invention.
Figure 11:
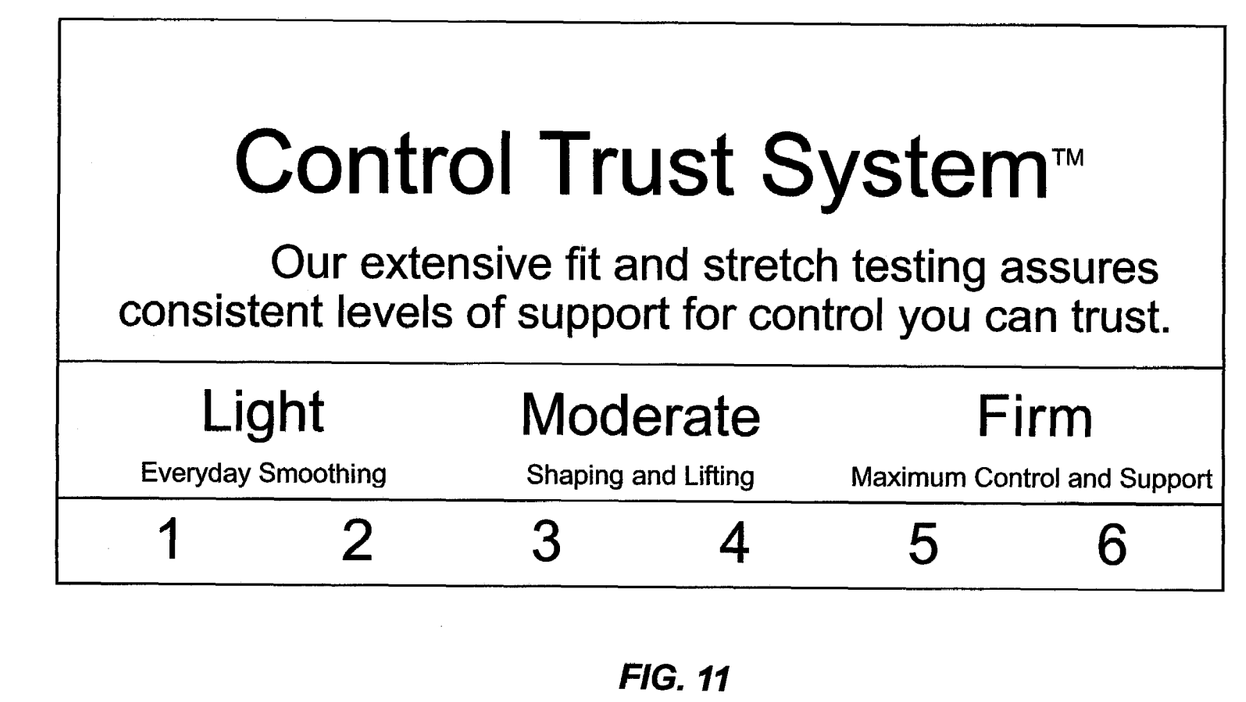
FIG. 11 illustrates an example of a label that would appear on the panty packaging at the point-of-sale to reflect the new support classification system according the present invention.

Referring to FIG. 10a, the different sizes and styles are classified in the current classification system. Referring to FIG. 10b, the different sizes and styles are classified in the new classification system represented by numbers 1 through 6. As shown in this Figure, a number of styles, such as 0374 and 0375, were originally classified as firm support, whereas after tested according to the present invention, styles 0374 and 0375 are actually moderate support. Referring to FIG. 11, new packaging reflects the new classification system and the categories or type of support for each category.

The system provides an elongation to consumers of proper levels of control, for Santoni and cut/sew garments, more especially panties and all-in-one undergarments. Thus superior comfort, fit and style are achieved and accurately categorized and classified. This is achieved by the control system with clearly measurable, consistent standards.

The present invention has been described with particular reference to the preferred embodiment. It should be understood that the foregoing descriptions and examples are only illustrative of the present invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

We claim:

1. A clamp system for a constant rate of extension machine comprising:
   a first clamp secured to a base of the machine; a second clamp secured to the base of the machine; wherein each of said first and second clamps further comprise
   a securing arm having a first end secured to the base;
   a second arm extending from a second end of said securing arm and perpendicular to said securing arm;
   a third arm extending from said second arm parallel to said securing arm; a fourth arm extending towards said securing arm and having a rounded head thereon;
   wherein said first clamp and said second clamp have an initial position and at least one of said first clamp and said second clamp moves with a predetermined rate and a predetermined force from said initial position.

2. The clamp system according to claim 1, wherein said first clamp and said second clamp are each C-shaped.

3. The clamp system according to claim 1 wherein said rounded heads of said first clamp and said second clamp are separated by a predetermined distance in said initial position.

4. The clamp system according to claim 1, wherein said predetermined distance is 254 mm.

5. A method for testing undergarment support in a constant rate of extension machine comprising:
   a. placing an undergarment on a first clamp portion of a first clamp and over a second clamp portion of a second clamp in the machine;
   b. causing said first clamp and said second clamp to move apart at a first predetermined rate and with a first predetermined force;
   c. sensing a force from the undergarment as said first clamp and said second clamp separate;
   d. causing said first clamp and said second clamp to move apart at a second predetermined rate and with a second predetermined force based upon said sensed force.

6. The method according to claim 5, further comprising before step a, securing said first clamp and said second clamp a predetermined distance apart.

7. The method according to claim 5, wherein steps a to d are repeated and each repetition measures another undergarment.

8. The method according to claim 5, wherein steps a to d are repeated to measure at least two different styles and sizes of undergarment.

9. The method according to claim 5, wherein said undergarment is placed at a midpoint of a top of a waist band and a top of a leg hole on said first clamp portion.

10. The method according to claim 5, wherein said undergarment is placed at a predetermined distance from a waist band and a top of a leg hole on said first clamp portion.

11. The method according to claim 9, wherein said predetermined distance is 4 inches.

12. The method according to claim 7, further comprising collecting data representing force against said first and second clamps as said first and said second clamps move apart.

13. The method according to claim 12, further comprising collecting data representing elongation of the undergarment between said first and said second clamps as said first and second clamps move apart.

14. The method of testing according to claim 13, further comprising manipulating said collected data to form elongation classifications for the undergarment.

15. The method according to claim 6, wherein said predetermined distance is 254 mm.

16. The method according to claim 5, wherein said first predetermined rate is 350 mm/min and said first predetermined force is 0.1 kg.

17. The method according to claim 5 wherein said second predetermined rate is 508 mm/min and said second predetermined force is 4.0 kg.

18. The method according to claim 5, wherein said undergarment is a woman's panty.

19. The method according to claim 18, wherein said panty is prepared according to testing criteria.

20. The method according to claim 19, wherein said panty is relaxed on a flat surface at a standard atmospheric condition of 70° F.±2° F. temperature (or 21° C.±1° C.) and 65%±2% relative humidity for at least four hours.

* * * * *